(12) United States Patent
Seguin

(10) Patent No.: US 7,270,824 B2
(45) Date of Patent: Sep. 18, 2007

(54) CITRULLINYLARGININE DIPEPTIDE ANALOGS AND THEIR DERMATOLOGICAL USES AS CARE AND TREATMENT AGENTS

(75) Inventor: Marie-Christine Seguin, Principality of Monaco (MC)

(73) Assignee: Exsymol S.A.M., Monaco (MC)

( * ) Notice: Subject to any disclaimer, the term of this patent is extended or adjusted under 35 U.S.C. 154(b) by 511 days.

(21) Appl. No.: 10/801,592

(22) Filed: Mar. 17, 2004

(65) Prior Publication Data

US 2004/0175397 A1   Sep. 9, 2004

Related U.S. Application Data

(62) Division of application No. 10/404,058, filed on Apr. 2, 2003, now Pat. No. 6,905,690.

(30) Foreign Application Priority Data

Apr. 5, 2002   (MC) .................................... 002484

(51) Int. Cl.
*A61K 35/80*   (2006.01)
*A61K 7/42*    (2006.01)

(52) U.S. Cl. .................................... 424/195.17; 424/59

(58) Field of Classification Search ........... 424/195.17, 424/59
See application file for complete search history.

(56) References Cited

U.S. PATENT DOCUMENTS 5,508,033 A    4/1996   Briand
6,716,436 B1 *  4/2004   Seguin ........................ 424/401

FOREIGN PATENT DOCUMENTS

EP        1060739       12/2000
NL        1006139       2/1999

OTHER PUBLICATIONS

Ito et al., "Amino Acid Composition of the Ethanolic Extractives From 31 Species of Marine Red Algae," 16 *J. Fisheries and Animal Husbandry* 77-90 (1977)(Abstract).
Laycock et al., "The Occurrence and Seasonal Variation of Gigartinine and L-Citrullinyl-L- Arginine in Chondrus-Crispus," 55 *Canadian J. of Biochem.* 27-30 (1977)(Abstract).

* cited by examiner

*Primary Examiner*—Christopher R Tate
*Assistant Examiner*—Randall Winston
(74) *Attorney, Agent, or Firm*—James C. Lydon

(57) ABSTRACT

The present invention relates to an algal adduct of the citrullinylarginine natural dipeptide as well as to its dermatological use and the use of chemical analogs issued from the same dipeptide displaying no toxic potential, as skin and phanera care and treatment agents, the said analogs having the following general formula (I):

$$H_2N-\underset{O}{\underset{\|}{C}}-NH-(CH_2)_3-\underset{NH-R_1}{\underset{|}{CH}}-\underset{O}{\underset{\|}{C}}-NH-\underset{C(=O)R_2}{\underset{|}{CH}}-(CH_2)_3-NH-\underset{NH-R_3}{\underset{\|}{C}}=NH \quad (I)$$

in which:
$R_1$ represents an acyl or acycloxy radical,
$R_2$ represents a hydroxyl, amine, alkylamine or alcoxy radical,
$R_3$ represents a hydrogen atom or a hydroxyl radical.

6 Claims, No Drawings

CITRULLINYLARGININE DIPEPTIDE ANALOGS AND THEIR DERMATOLOGICAL USES AS CARE AND TREATMENT AGENTS

This application is a division of U.S. patent application Ser. No. 10/404,058, filed Apr. 2, 2003 now U.S. Pat. No. 6,905,690.

The present invention relates to an algal adduct of the citrullinylarginine natural dipeptide as well as to its dermatological use and the use of chemical analogs issued from the same dipeptide as skin and phanera care and treatment agents.

The literature reports the property shared to macroalgae to consume nitrogen from the external sources located in the sea such as nitrate, nitrite or ammonium ions, to reduce it and finally to stock it as organic form especially as amino acids, proteins and pigments (Hanisak M. D (1983), In Capenter, E. J. and Capone, D. G (Eds) "Nitrogen in the marine environment". Academic press Inc.).

Thus, it has been isolated and structurally characterized from a Grateloupia turuturu red seaweed extract and for the first time a nitrogenous organic model under the form of the citrullinylarginine dipeptide (Miyazawa K. and al., Bulletin of the Japanese Society of Scientific Fisheries (1974), vol.40, pp.815-818).

Other rhodophyceae such as *Grateloupia filicina, Polyides rotundus, Polysiphonia lanosa* have been later on identified with the occurrence of the same dipeptide in the composition of their alcoholic extracts, and more specifically in *Chondrus crispus* red alga. When this seaweed is for instance collected off Canada at the end of the winter season, the citrullinylarginine dipeptide represents the main nitrogenous organic model and contains more than 50% of the total nitrogen available in the plant (Laycok M. V. and al., Can. J. Biochem. (1977), vol.55, pp.27-30).

Then new studies on *Chondrus crispus* alga, led by the same canadian scientific searchers' group, however evidenced the influence of others physiological factors than the nitrogen bioavailability of canadian coastal waters in the conditions of natural production of the citrullinylarginine dipeptide in the alga (Laycock M. V and al., Can. J. Biochem. (1981), vol.59, pp.522-527). They thus noticed that the citrullinylarginine contents were fluctuating during the year with a molecule storage process mainly during the winter season and when the water temperature is less than 15° C. The highest dipeptide concentration is moreover reached at the end of the winter season. The same authors also underlined the vegetative stage of the plant during that storage process, the growth being limited because of cold waters. Finally, a minimum of radiation or light intensity is definitely needed in that process.

The authors of above-mentioned works however only propose for the stored dipeptide a role of nitrogen potential reserve which is energetic for the plant. This reserve is indeed available then quickly consumed as soon as external nitrogenous source concentrations located in the sea are lowered, specifically when the spring season is back. The dipeptide therefore supports the plant and allows it to take fully advantage of favourable conditions for its growth.

The dermatological use of the citrullinylarginine dipeptide as a skin and phanera care and treatment agent was considered by the applicant for several reasons.

First of all, the literature does not report the biosynthesis of such a contribution under this form within cutaneous tissues and phanera of upper mammals. Then, because of the structure and the number of nitrogen atoms of the citrullinylarginine dipeptide, such a contribution is likely to constitute, following its noticed behaviour in the alga, a rather important nitrogen source, which is interesting for instance to the skin in the healing and repairing process of cutaneous tissues. Indeed, a nitrogen loss is normally noticed during the post-traumatic period (Chyun J. H. and al., J. Nutr. (1984), vol.114., pp.1697-1704). Acidosis problems of a perturbed skin and the maintain of the intracellular neutral pH with such a nitrogen source are also targeted.

The dipeptide interest as a skin and phanera care and treatment agent also results from its biological properties discovered by the applicant and described in the following detailed description of the invention. The positive action of the citrullinylarginine dipeptide on the energetic metabolism of fibroblasts in culture and a cytostimulating behaviour have been evidenced respectively through an adenosine triphosphate dosage and a cell proliferation test.

Correlatively to the physiological role held by the dipeptide in the alga and on the basis of a known over-expression of chaperones' proteins (Heat Shock Proteins or HSP) in reply to a negative thermal shock (Holland D. B. and al., J. Invest. Dermatology (1993), vol.101, pp.196-199), the applicant demonstrated the interest of using the dipeptide at cutaneous level to treat a skin exposed to a cold temperature. In these unfavourable conditions, the energetic reserve constituted by the citrullinylarginine molecule improves the synthesis of proteins at epidermic cell level and enhances the expression of chaperones' proteins.

The applicant also evidenced the interest of the dipeptide to treat a skin exposed to a reduced light intensity without increase of the atonicity and the loss of cutaneous sparkle.

Besides, on a second level, the citrullinylarginine dipeptide can be used as a citrulline and arginine source under the action of skin proteases as the dipeptide cutaneously penetrates.

An exogenous contribution of these two aminoacids and especially of arginine is also of an interest in dermatology. Arginine is thus greatly induced in the healing process because of its antioxidant character. It is too described as a substrate in the collagen synthesis (Chithra P. and al., J. Clin. Biochem. Nutr. (1995), vol.18, pp.111-117 and cited references).

The occurrence of citrulline is encountered in some epidermic proteins (Kubilus J. and al., Biochim. Biophys. Acta (1979), vol.581, pp.114-121) and in some hair proteins (Rogers G. E. and al., Biochim. Biophys. Acta (1977), vol.495, pp.159-175), after an enzymatic conversion of side-arginine residues. Arginine and citrulline are known as metabolic intermediates in the urea cycle. An over-production of endogenous urea is looked for in dry skin problems (Wolhrab J., Skin Pharmcol. Appl. Skin Physiol. (2002), vol.15, pp.44-45).

Nevertheless, unexpectedly and highly surprisingly, the applicant noticed the genotoxic potential of said dipeptide both for the purified substance extracted from Chondrus crispus alga and for a nature identical obtained by chemical synthesis.

Those two results come from investigations achieved by the applicant according to OECD 471 guidelines, with the respect of a current well-established method in the search of mutagenic potential for any administrable form in human: the Ames test (Kirkland D. J., Mutation research (1994), vol.312, pp.195-199, (ICH steering committee, 19 Jul. 1995, Guidance on specific aspect of regulatory genotoxicity tests of pharmaceuticals).

It is therefore obvious that such a behaviour is absolutely not compatible with any use in dermatology of the citrullinylarginine dipeptide.

The researchers of the present invention have then kept on working theirs searches with works aiming at the obtention of citrullinylarginine forms but devoid of genotoxic potential while keeping the whole of activities originally demonstrated for the dipeptide.

The applicant thus identified various synthetic dipeptides. They were partially or totally functionalized on three of their potential substitution sites. They have the same biological properties as the ones noticed for the purified natural substance. On the other hand, such structures do not display the above-mentioned unacceptable side-effect.

In a parallel way, the applicant noticed the removal of the genotoxic character for an algal extract enhanced with polypeptides or proteins and obtained according to the hereafter protocol developed by the inventors of the present invention.

The first purpose of the invention is thus to obtain an analog of the natural dipeptide, from algal origin too but in which there is no genotoxic potential relevant to the purified natural molecule. The biological properties noticed in this latter are nevertheless totally maintained.

The first step of the protocol is a seaweed extraction, notably from red macroalgae, preferably from Chondrus crispus, with the help of a solvent or a solvent mixture acceptable in pharmacy.

The said alga is preferably a seaweed having stored optimally 10% in dry weight of citrullinylarginine as compared to the dry seaweed total weight.

The extraction process used in order to obtain the extract as purpose of the invention is advantageously applied with conditions such as the said extraction is performed at reflux of said solvent or solvent mixture during 2 to 4 hours.

Preferred solvent for the said extraction is a mixture of water with ammoniacal ethanol.

The second step aims at enhancing the weight amount of intrinsic polypeptides or proteins up to a total content equal to at least 20%.

According to an interesting embodiment of the invention, the enhancement comes from a concentration of intrinsic native proteins. Alternatively, the enhancement can be extrinsic and comes from the incorporation of standard proteins available in pharmacy.

The incorporated proteins will be preferably plant proteins or their hydolysates, such as notably wheat or soya proteins.

While conforming with current regulations in effect, the incorporated proteins will be preferably animal proteins or their hydrolysates, such as collagen or elastin.

The incorporated proteins will be preferably marine collagen or its hydrolysate.

The incorporated proteins will be preferably other algal proteins or their hydrolysates, such as notably spiruline and microalgal proteins.

Eventually, some titrated citrullinylarginine dipeptide obtained by chemical way can be incorporated to the obtained extract in order to supplement the said extract up to 10% in weight.

The third step is a treatment in hot of said extract enhanced with polypeptides or proteins.

The said treatment is advantageously performed during 3 hours at 40° C.

Undeniably, due to its negative result to the Ames test, the said analog obtained from the protocol described here above represents a new structurally product. It is different from the purified natural molecule, probably because of its adduct state and of the occurrence of many interactions with said polypeptides or proteins.

A second purpose of the invention concerns the use of this algal adduct, more commonly called extract, as well as the use of citrullinylarginine chemical analogs devoid of genotoxic potential, as skin and phanera care and treatment agents.

A care and treatment agent is described in the meaning of the present invention as agents which generally display repairing and revitalizing properties enabling them to react better against damaging effects such as cold or darkness.

As far as we know to date, no use of the citrullinylarginine dipeptide or of its partially or totally chemical fonctionalized analogs has been claimed for such purposes.

The international patent application published under the WO94/09750 number describes a cosmetic composition based on arginine and citrulline peptide derivatives. Some dipeptide derivatives were largely disclosed in that application. Listed structures are nevertheless different from the ones object of the invention because of a different position of the peptidic bound, as well as developed properties.

The cosmetic use of citrullinylarginine chemical analogs were nevertheless already described in a previous patent application filed by the applicant and published under the EP 1 060 739 A1 number. This discloses a cosmetic composition for slimming containing L-arginine, an L-arginine analog, or one of theirs derivatives, for topical application. But again properties currently developed at skin and phanera levels by the same analogs according to the invention are neither mentioned nor even suggested in that previous document.

The research of a structure/activity relationship led by the applicant on the said chemical analogs revealed that a main condition for the loss of genotoxic potential is the replacement of the α-amino function within the citrulline unit.

The replacement of the α-carboxy and guanido functions within the arginine unit has also been considered. While keeping the character of non toxicity, the replacement however appeared more secondary allowing rather a better efficiency of said analogs to claimed applications.

This is why another purpose of the present invention is also the dermatological use of analogs of citrullinylarginine natural dipeptide, or one of any of their salts, as skin and phanera care and treatment agents, said analogs having the following general formula (I):

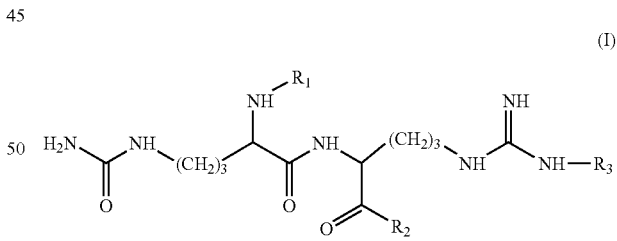

in which:
R$_1$ represents an acyl or acycloxy radical,
R$_2$ represents a hydroxyl, amine, alkylamine or alcoxy radical,
R$_3$ represents a hydrogen atom or a hydroxyl radical.

Like the extract from algal origin previously described, all those derivatives are not potentially genotoxic. Their dermatological use is consequently totally acceptable.

Those derivatives are simply synthesized following methods known by the person skilled in the art, namely for instance through acylation of the α-amino function and/or esterification of the α-carboxylic function.

According to an embodiment of the invention, the compound of general formula (I) is such that $R_1$ is an acyl or acyloxy radical, advantageously an acetyl radical, $R_2$ is an alcoxy radical, advantageously an ethyloxy radical, and $R_3$ is an atom of hydrogen.

Another embodiment of the invention is to use a compound of general formula (I) in which $R_1$ is an acyl or acyloxy radical, advantageously an acetyl radical, $R_2$ is a hydroxyl radical, and $R_3$ is an atom of hydrogen.

The following examples constitute a non-restrictive list of said analogs according to the invention.

N-acetyl-L-citrullinyl-L-arginine ethyl ester (NAc-L-CIT-L-ARG-OEt)

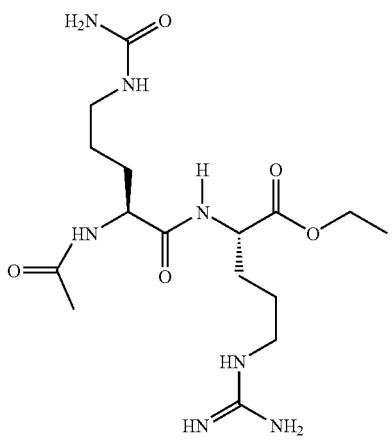

N-acetyl-L-citrullinyl-L-arginine (NAc-L-CIT-L-ARG)

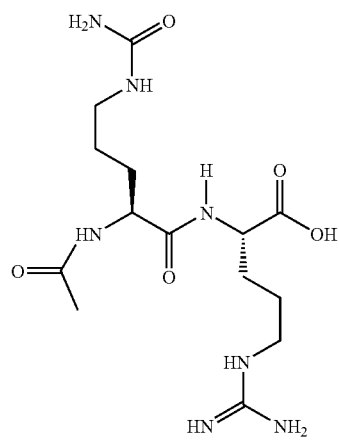

As it was already mentioned, the citrullinylarginine molecule notably displays an activity on the cell energetic metabolism. It has also some cytostimulating properties as well as a potentiating action on the expression of chaperones' proteins aiming at improving the behaviour of a skin or phanera exposed to a cold temperature.

Several in vitro tests were performed in order to compare the activities of the purified natural dipeptide described beforehand with activities of the algal adduct which was the first purpose of the invention, and with activities of some chemical analogs, other purpose of the invention.

The following tests illustrate those comparative data.

Test 1: influence of analogs of the citrullinylarginine natural dipeptide on the energetic metabolism of cultured fibroblasts through a triphosphate adenosine (ATP) dosage. Comparison with the purified natural dipeptide.

The fibroblasts cells are cultivated and seeded at a rate of $10^5$ cells/ml in the presence of a growth factor-deprived medium (2% fetal calf serum).

On each cell suspension, the ATP quantity is measured by photometry, by establishing the decrease of absorbance at 340 nm according to following specific equations:

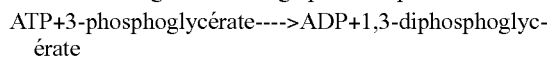
ATP+3-phosphoglycérate---->ADP+1,3-diphosphoglycérate

1,3-diphosphoglycérate+NADH---->glycéraldéhyde-3-P+NAD+P

Results:

|  | ATP quantity (nM/mg proteins) |
|---|---|
| A (control without active ingredient) | 26.7 +/− 5.2 |
| A + 1% purified Cit-Arg | 88.62 +/− 8 |
| A + 1% algal adduct | 96.2 +/− 6.2 |
| A + 1% NAc-Cit-Arg | 90.7 +/− 6.5 |

Test 2: evidence of the cytostimulating properties of the citrullinylarginine natural dipeptide analogs.

The test was performed on a human fibroblast cell line maintained in a culture medium filed with 2% fetal calf serum.

The assessment of the cell proliferation is carried out through a neutral red colorimetric test (Borenfreund E. and al. (1984), Toxicol. Lett., vol.24, pp.119). Cell growth variation is then obtained by measuring optical density (OD) at 540 nm, following the specific equation:

$$\% \text{ stimulation} = \frac{OD_{\text{active ingredient}} - OD_{\text{control}}}{OD_{\text{control}}} * 100$$

Results:

| purified Cit-Arg (%) | 0.016 | 0.031 | 0.063 | 0.125 | 0.5 |
|---|---|---|---|---|---|
| % stimulation | 2 | 25 | 30 | 32.5 | 36 |
| algal adduct (%) | 0.016 | 0.031 | 0.063 | 0.125 | 0.5 |
| % stimulation | 8 | 32 | 38 | 44 | 52 |
| NAc-Cit-Arg (%) | 0.016 | 0.031 | 0.063 | 0.125 | 0.5 |
| % stimulation | 5 | 26 | 34 | 40 | 45 |

Test 3: action of analogs of the citrullinylarginine natural dipeptide on the expression of chaperones' proteins (HSP 72) at a cold temperature. Comparison with the purified natural dipeptide.

Some reconstituted human epidermis were exposed to a 4° C. temperature, first without active ingredient (control) and then with the presence of the active ingredient to test. The assessment of HSP 72 expression was semi-quantitatively detected by immunofluorescence using a HSP 72-specific monoclonal antibody. It is based on a global assessment of the observed fluorescence. The more the fluorescence is important, the more the HSP 72 proteins are expressed.

Results:

|  | control | purified Cit-Arg | algal adduct | NAc-Cit-Arg |
|---|---|---|---|---|
| HSP 72 | ++ | +++ | ++++ | +++ |

++: few cells are fluorescent
+++: many cells are fluorescent
++++: the whole living cell layers are fluorescent The interest of the dipeptide or its chemical analogs for treating a skin exposed to a reduced light intensity was demonstrated through an in vivo test performed on a panel of men and women. The test was carried out with the algal adduct which was included in the composition of a cream detailed hereafter, in combination with some light therapy sessions.

Test 4: cutaneous action of a cream prepared with 7% of algal adduct in combination with some light therapy sessions The assessment technique of such an effect at skin level was this one of self-assessment technique through analogical scale.

Two series of light therapy sessions were thus conducted:
first series: ten persons had to notice each parameter defined by the applicant, before and after a specific number of sessions with following exposure conditions:
Light intensity: 2500 Lux
Exposure time: 20 mn a day
Treatment prescription: twice a week during a month
second series: the above ten persons had to notice the same parameters with same light exposure conditions as already mentioned and after having applied topically a cream prepared with 7% of algal extract.

Formulation of the composition containing the said extract:

| glyceryl stearate and steareth | 10 |
|---|---|
| cetearylethylhexanoate | 10 |
| macadamia ternilolia seed oil | 10 |
| glycerol | 3 |
| dimethicone | 0.3 |
| sodium methylparaben | 0.1 |
| propylparaben | 0.05 |
| imidazolidinylurea | 0.3 |
| polyacrylamide and C13-14 isoparaff in and laureth 7 | 1 |
| Chondrus extract (titrated at 10% in citrullinylarginine) | 7 |
| purified water qsp | 58.05 |

Results:

For 80% of tested persons, a significant improvment of the moisturizing was noticed giving rise a pleasant and uniform touch. For 70% of them, there was a back to a cutaneous sparkle, in particular of the face, integrated with dermic deep layers reducing the atonicity of skin.

Another purpose of the invention is also the use of the adduct algal and of citrullinylarginine chemical analogs as defined here above, in or for the preparation of dermatological compositions.

The invention claimed is:

1. A method for repair and/or revitalization of the skin or phanera of a mammal in need of said repair and/or revitalization,
comprising topically administering to said mammal a composition prepared by a process comprising:
extracting a natural citrullinylarginine dipeptide from algae into a pharmaceutically acceptable solvent or solvent mixture to form an extract;
enhancing an amount of intrinsic polypeptides or proteins present in said extract up to a total content equal to at least 20%, by concentrating said mixture and/or by adding additional amounts of the polypeptides or proteins to said extract;
heat treating said extract to produce a non-genotoxic analog of said citrullinylarginine dipeptide; and
adding said extract to an acceptable carrier; said composition comprising said analog of said citrullinyularginine dipeptide.

2. The method of claim 1, wherein said composition is administered as a potential nitrogen source.

3. The method of claim 1, wherein said composition is administered to activate the energetic cell metabolism.

4. The method of claim 1, wherein said composition displays cytostimulating properties.

5. The method of claim 1, wherein said composition is administered to skin or phanera which has been exposed to a cold temperature.

6. The method of claim 1, wherein said composition is administered to allow the skin to withstand a reduced light intensity without increasing atonicity and loss of cutaneous sparkle.

* * * * *